United States Patent
Girrell et al.

(10) Patent No.: US 10,444,194 B2
(45) Date of Patent: Oct. 15, 2019

(54) METHOD AND APPARATUS FOR MATERIAL IDENTIFICATION OF PIPELINES AND OTHER TUBULARS

(71) Applicant: Microline Technology Corporation, Traverse City, MI (US)

(72) Inventors: Bruce I. Girrell, Traverse City, MI (US); Dean M. Vieau, Traverse City, MI (US); Johana M. Chirinos, Traverse City, MI (US); Douglas W. Spencer, Rapid City, MI (US); Trenton M. Bruce, Traverse City, MI (US); Jabin D. Reinhold, Traverse City, MI (US)

(73) Assignee: QUANTA ASSOCIATES, L.P., Houston, TX (US)

( * ) Notice: Subject to any disclaimer, the term of this patent is extended or adjusted under 35 U.S.C. 154(b) by 148 days.

(21) Appl. No.: 15/495,108

(22) Filed: Apr. 24, 2017

(65) Prior Publication Data

US 2017/0307500 A1    Oct. 26, 2017

Related U.S. Application Data

(60) Provisional application No. 62/327,645, filed on Apr. 26, 2016.

(51) Int. Cl.
*G01N 29/04* (2006.01)
*G01N 29/265* (2006.01)
(Continued)

(52) U.S. Cl.
CPC .......... *G01N 29/04* (2013.01); *G01N 29/11* (2013.01); *G01N 29/265* (2013.01); *G01N 27/02* (2013.01);
(Continued)

(58) Field of Classification Search
CPC .... G01N 15/08; G01N 3/40; G01N 2291/262; G01N 27/02; G01N 27/72; G01N 29/04
(Continued)

(56) References Cited

U.S. PATENT DOCUMENTS 2,814,019 A    11/1957  Bender
3,667,035 A     5/1972  Slichter
(Continued)

FOREIGN PATENT DOCUMENTS

CA          2631884        1/2009

OTHER PUBLICATIONS

Pavlina et al., "Correlation of Yield Strength and Tensile Strength with Hardness for Steels," ASM International, vol. 17(6), Dec. 2008.
(Continued)

*Primary Examiner* — Marrit Eyassu
(74) *Attorney, Agent, or Firm* — Honigman LLP

(57) ABSTRACT

A material property determining system operable to determine properties of a conduit. The material property determining system includes a tool movable along a conduit and having at least one sensing device for sensing at least one property of the conduit. A processor is operable to process outputs of the at least one sensing device. Responsive to processing of the outputs by the processor, the processor correlates the processed outputs to determine the type of material of the conduit.

14 Claims, 12 Drawing Sheets

1 – Module
2 – Module
3 – Module
4 – Universal Joint
5 – Drive Cup, Centralizer, and/or Cleaning Ring
6 – Tubular Exemplar of a Tool with Multiple Modules within a Tubular

(51) Int. Cl.
*G01N 29/11* (2006.01)
*G01N 27/72* (2006.01)
*G01N 27/02* (2006.01)
*G01N 27/90* (2006.01)

(52) U.S. Cl.
CPC .......... *G01N 27/72* (2013.01); *G01N 27/725* (2013.01); *G01N 27/902* (2013.01); *G01N 2291/2636* (2013.01)

(58) Field of Classification Search
USPC .......................................................... 73/38
See application file for complete search history.

(56) References Cited

U.S. PATENT DOCUMENTS

| | | | |
|---|---|---|---|
| 3,942,373 A | 3/1976 | Rogers | |
| 3,994,163 A | 11/1976 | Rogers | |
| 4,105,071 A | 8/1978 | Nicolas et al. | |
| 4,207,765 A | 6/1980 | Kiff | |
| 4,351,186 A | 9/1982 | Moulin | |
| 4,352,065 A | 9/1982 | Rogachev et al. | |
| 4,408,160 A | 10/1983 | King et al. | |
| 4,444,050 A | 4/1984 | Revett | |
| 4,543,827 A | 10/1985 | Tominaga et al. | |
| 4,708,204 A | 11/1987 | Stroud | |
| 4,719,803 A | 1/1988 | Capelle et al. | |
| 4,766,764 A | 8/1988 | Trevillion | |
| 4,966,234 A | 10/1990 | Whitten | |
| 5,004,724 A | 4/1991 | De | |
| 5,166,613 A | 11/1992 | Perry | |
| 5,172,480 A | 12/1992 | Labuc et al. | |
| 5,313,405 A | 5/1994 | Jiles et al. | |
| 5,375,476 A | 12/1994 | Gray | |
| 5,520,245 A | 5/1996 | Estes | |
| 5,532,587 A | 7/1996 | Downs et al. | |
| 5,537,035 A | 7/1996 | Fowler et al. | |
| 5,619,135 A | 4/1997 | Kohn et al. | |
| 5,681,995 A | 10/1997 | Ooura et al. | |
| 5,720,345 A | 2/1998 | Price et al. | |
| 5,828,211 A | 10/1998 | Scruby et al. | |
| 6,133,731 A | 10/2000 | Melamud et al. | |
| 6,243,657 B1 | 6/2001 | Tuck et al. | |
| 6,288,535 B1 | 9/2001 | Chass | |
| 6,523,428 B2 | 2/2003 | Kaji | |
| 6,583,617 B2 | 6/2003 | LeVert et al. | |
| 6,851,476 B2 | 2/2005 | Gray et al. | |
| 6,854,336 B2 | 2/2005 | Buttle | |
| 6,904,806 B2 | 6/2005 | Pryor | |
| 6,924,640 B2 | 8/2005 | Fickert et al. | |
| 7,038,444 B2 | 5/2006 | Crouch et al. | |
| 7,116,182 B2 | 10/2006 | Varsamis et al. | |
| 7,128,988 B2 | 10/2006 | Lambeth | |
| 7,141,968 B2 | 11/2006 | Hibbs et al. | |
| 7,150,317 B2 | 12/2006 | Barolak et al. | |
| 7,159,470 B2 | 1/2007 | Saguto | |
| 7,259,555 B2 | 8/2007 | Nummila et al. | |
| 7,403,000 B2 | 7/2008 | Barolak et al. | |
| 7,443,168 B2 | 10/2008 | Gold et al. | |
| 7,454,657 B2 | 11/2008 | Duron et al. | |
| 7,595,636 B2 | 9/2009 | Barolak et al. | |
| 7,660,197 B2 | 2/2010 | Barolak | |
| 7,795,864 B2 | 9/2010 | Barolak et al. | |
| 8,035,374 B1 | 10/2011 | Girrell et al. | |
| 8,760,638 B2 | 6/2014 | Imai et al. | |
| 8,797,033 B1* | 8/2014 | Girrell | E21B 47/0006 324/309 |
| 8,913,251 B2 | 12/2014 | Tin | |
| 8,941,821 B2 | 1/2015 | Coupe et al. | |
| 9,134,121 B2 | 9/2015 | Tin et al. | |
| 9,170,194 B2 | 10/2015 | Ichizawa et al. | |
| 2002/0024337 A1 | 2/2002 | LeVert et al. | |
| 2004/0113627 A1 | 6/2004 | West et al. | |
| 2006/0164091 A1* | 7/2006 | Nestleroth | G01N 27/902 324/326 |
| 2006/0201253 A1 | 9/2006 | Gonzales | |
| 2007/0012111 A1 | 1/2007 | Kim | |
| 2007/0022830 A1 | 2/2007 | Mandziuk et al. | |
| 2008/0302187 A1 | 12/2008 | Huber et al. | |
| 2009/0003130 A1 | 1/2009 | Barolak | |
| 2009/0168599 A1 | 7/2009 | Suarez et al. | |
| 2010/0179413 A1 | 7/2010 | Kadour et al. | |
| 2011/0167914 A1* | 7/2011 | Sutherland | F17D 1/00 73/643 |
| 2012/0143522 A1 | 6/2012 | Chen et al. | |
| 2012/0143523 A1 | 6/2012 | Chen et al. | |
| 2012/0143525 A1 | 6/2012 | Chen et al. | |
| 2012/0288049 A1 | 11/2012 | Renshaw et al. | |
| 2012/0307250 A1 | 12/2012 | Wang et al. | |
| 2013/0335745 A1 | 12/2013 | Sano | |
| 2014/0116715 A1 | 5/2014 | Sipila et al. | |
| 2016/0084076 A1* | 3/2016 | Fanini | E21B 47/12 340/853.1 |
| 2016/0231277 A1 | 8/2016 | Molenda et al. | |
| 2017/0102479 A1* | 4/2017 | Kouchmeshky | E21B 47/102 |

OTHER PUBLICATIONS

Amend, "Using Hardness to Estimate Pipe Yield Strength; Field Application of ASME CRTD—vol. 91," Proceedings of the 2012 9th International Pipeline Conference IPC2012, Sep. 24-28, 2012, Calgary, Alberta, Canada.

* cited by examiner

Exemplar of a Tool with Multiple Modules within a Tubular with Robotic Crawling Propulsion Capabilities 1 – Module
2 – Module
3 – Module
4 – Universal Joint
5 – Tracked Drive
6 – Pull Loop
7 – Pull Cable and/or Powered/ Communications Cable
8 – Tubular Exemplar of a Tool with Multiple Modules within a Tubular with Push and/or Pull Propulsion Capabilities 1 – Module
2 – Module
3 – Module
4 – Universal Joint
5 – Centralizer
6 – Pull Loop
7 – Pull Cable and/or Powered/Communications Cable
8 – Coiled Tube (Push)
9 – Tubular Real-Time Data Processing and Classifying

METHOD AND APPARATUS FOR MATERIAL IDENTIFICATION OF PIPELINES AND OTHER TUBULARS

CROSS REFERENCE TO RELATED APPLICATION

The present application claims the filing benefits of U.S. provisional application Ser. No. 62/327,645, filed Apr. 26, 2016, which is hereby incorporated herein by reference in its entirety.

FIELD OF THE INVENTION

The present invention relates to generally to a method of detecting properties of a pipeline or conduit or tubular via a tool or device that is moved along and within the pipeline or conduit or tubular.

BACKGROUND OF THE INVENTION

It is known to use a sensing device to sense or determine the strength of and/or freepoints and/or stresses in pipes and other tubulars. Examples of such devices are described in U.S. Pat. Nos. 4,708,204; 4,766,764; 8,035,374 and/or 8,797,033.

SUMMARY OF THE INVENTION

The present invention provides a method and system and device that includes moving a tool or instrument along and within a pipe or well casing or conduit or tubular to collect data, and processing collected data to determine characteristics or properties of the pipe or conduit or tubular. The properties may be analyzed to determine or identify the material of the pipe or conduit or tubular or other properties such as hardness and/or permeability. The present invention may collect data via any one or more suitable sensing means, such as, for example, magneto-responsive sensing, electronic sensing, acoustic sensing and/or the like, with the collected data preferably providing information indicative of two or more physical properties of the conduit. The system processes the data and, responsive to such data processing (including correlating the two or more physical properties determined by the sensing technologies), is able to determine or predict or identify the material of the conduit or tubular along which the tool or instrument is moving. For example, the system may detect or sense and process data collected via Barkhausen noise methods, pulsed eddy current methods, remote field eddy current methods, low frequency AC methods, high frequency AC methods, impedance methods and/or acoustic methods (with the system sensing and collecting data associated with the pipe or conduit or tubular as the tool or device moves along and within the pipe or well casing or conduit or tubular) and may correlate the results of such data processing to provide an accurate determination or identification of the particular type of material of the conduit or tubular.

These and other objects, advantages, purposes and features of the present invention will become apparent upon review of the following specification in conjunction with the drawings.

DESCRIPTION OF THE PREFERRED EMBODIMENTS

Figure 1:
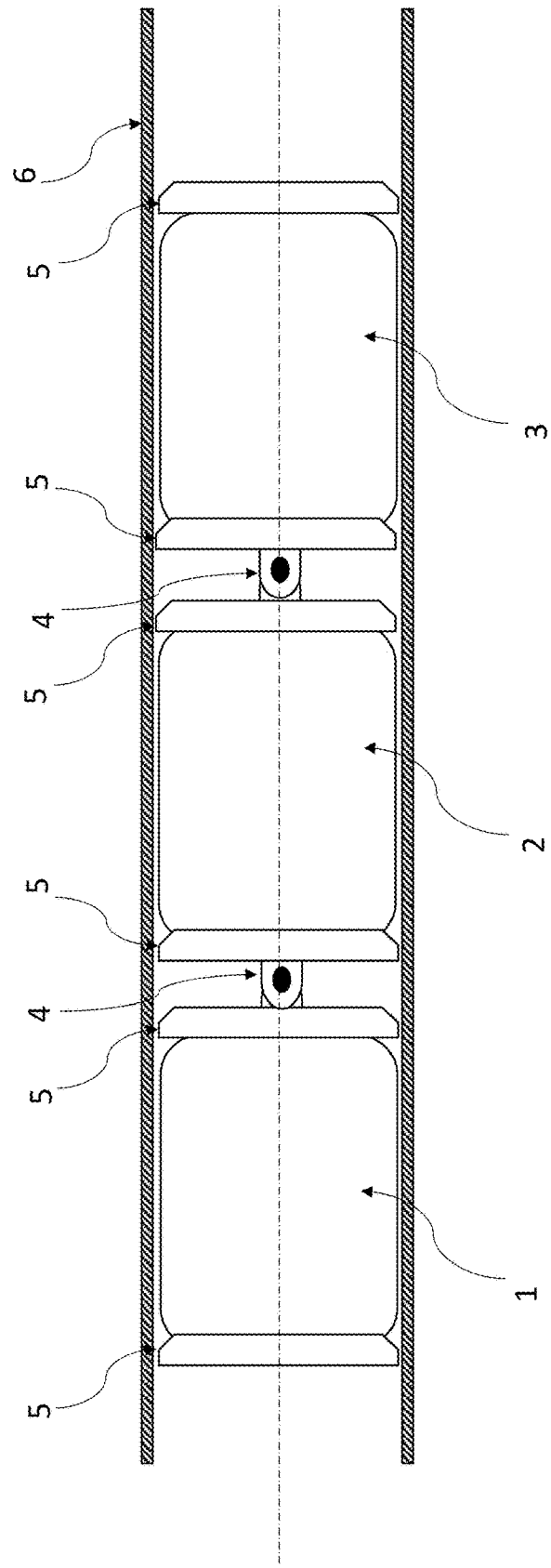
FIG. 1 shows a horizontal cross section of a pipe or tubular with a tool of the present invention disposed therein.

The present invention provides a system and method and apparatus for material identification of pipelines, well casings, and other tubulars or conduits. The tool can be operated in pipelines (e.g., inline inspection), downhole applications, and other tubulars for the purpose of material identification (MI) of the conduit material (such as steel or type/grade of steel or the like). The material identification (MI) is defined as one or more testing methods performed to verify and/or delineate grades of steel. Delineation of steel grades is accomplished via determining differences in mechanical material properties through various means such as, but not limited to, magnetic sensing means, acoustic sensing means, electrical sensing means and/or the like. For example, the mechanical material properties to be determined may include, but are not limited to, the yield strength, tensile strength, hardness and/or the like of the conduit material.

The sensing system of the present invention utilizes one or more tools that is/are moved along and in a tubular or conduit and that senses or collects data via one or more sensors. The tool senses two or more physical properties of the conduit, such that the determined physical properties can be correlated to determine or identify the material of the conduit. The tool (or two spaced apart tools) may include, for example, a magnetic flux leakage sensor and a magnetic Barkhausen noise sensor and/or a pulsed eddy current sensor. The system collects data sensed or collected by the sensors and processes the collected data to determine various characteristics of the tubular that each sensor methodology is capable of sensing and determining. The system then correlates the processed data to determine or identify the type of material that the tubular is made of.

The tool is operable to identify at least one material property and/or characteristic for material identification. The tool utilizes at least one sensing technology, or any combination of several sensing technologies, such as one or more of the technologies discussed below. The tool may utilize individual sensor(s) or array(s) unlimitedly disposed in uniform or non-uniform arrangements/patterns for any one or more of the sensing technologies.

For example, a given sensing methodology may be capable of determining hardness of a material and another sensing methodology may be capable of determining permeability of a material. Neither of these characteristics by themselves may positively identify a material (since different materials may have similar hardness or similar permeability). However, the system of the present invention uses both sensing methodologies and correlates the data to positively identify the material (since most materials will not have both the same hardness and the same permeability). For example, if a Magnetic Barkhausen sensor is used to determine a particular material hardness, the system may determine that the material is one of perhaps two or more types of materials that exhibit that hardness characteristic. Then, the system may look to the permeability measurements (such as measured or determined by a magnetic flux leakage (MFL) sensor, and determines which of the two or more types of materials (determined from the hardness measurements) also exhibit permeability characteristics similar to the permeability determined by the MFL sensor. By utilizing two or more sensing methodologies in this manner, the system can accurately determine or identify the particular material of the tubular.

The system thus provides a measure of yield strength and/or other aspects of physical properties, so the pipe can be identified to avoid potential failure as may occur when the pipe material is unknown or mis-identified. To avoid having to dig up and test pipes in the ground, the system of the present invention provides for data collection and analysis to identify with a high degree of confidence the material of the pipe via an inline inspection tool and methodology. The tool travels along pipe and makes measurements, and the system correlates data with yield strength of various materials and other characteristics or physical properties of materials to determine the pipe material. By measuring certain aspects of the pipe's properties, the system can identify pipes that are similar to one another and can determine the material of those pipes (by projecting testing results onto properties determined by the various sensing methodologies performed by a tool in a particular pipe). The system thus uses multiple technologies in parallel and correlates the collected data to better identify the material. The system can further increase the material identification confidence level by using more technologies/data.

The tool collects data and may store collected data on-board, or may transmit collected data to a remote location for storage (and/or processing), or the tool may perform a combination of both.

The tool employs advanced data processing techniques to isolate and extract useful data. For example, the tool may employ advanced data processing techniques that use a single sensing technology, or any combination of sensing technologies (together or individually). The data processing techniques may include a classifier/classification system and/or method, and the data processing may be performed on-board the tool, at a remote location, or a combination of both.

The data processing may utilize feature extraction and classification via software learning systems. Optionally, the data processing may employ binning techniques. Optionally, the data processing may be conducted in real-time during tool operation, off-loaded after completion of a tool operation, or a combination of both.

The tool of the present invention may comprise at least one module that is movably disposed in a conduit. The module may contain at least one sensing technology, or the module may contain multiple sensing technologies that interact with each other, and/or utilize shared componentry.

Figure 2:
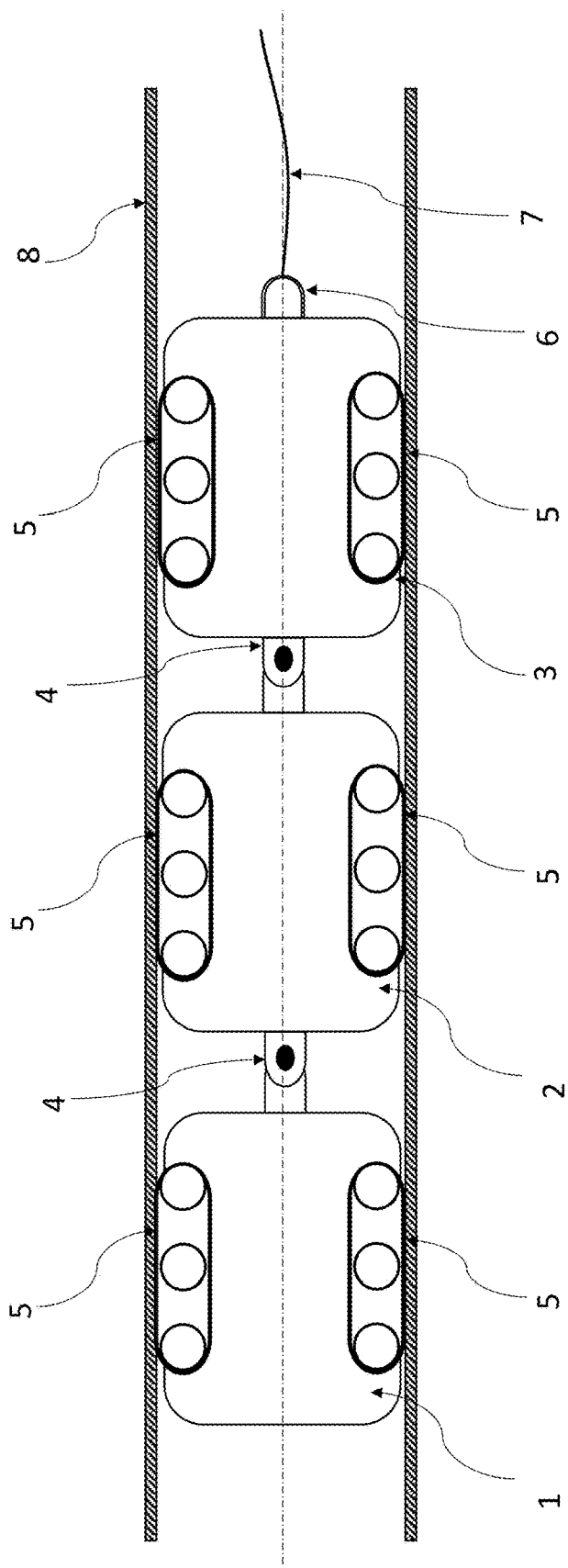
FIG. 2 shows a horizontal cross section of a pipe or tubular with another tool of the present invention disposed therein.
Figure 3:
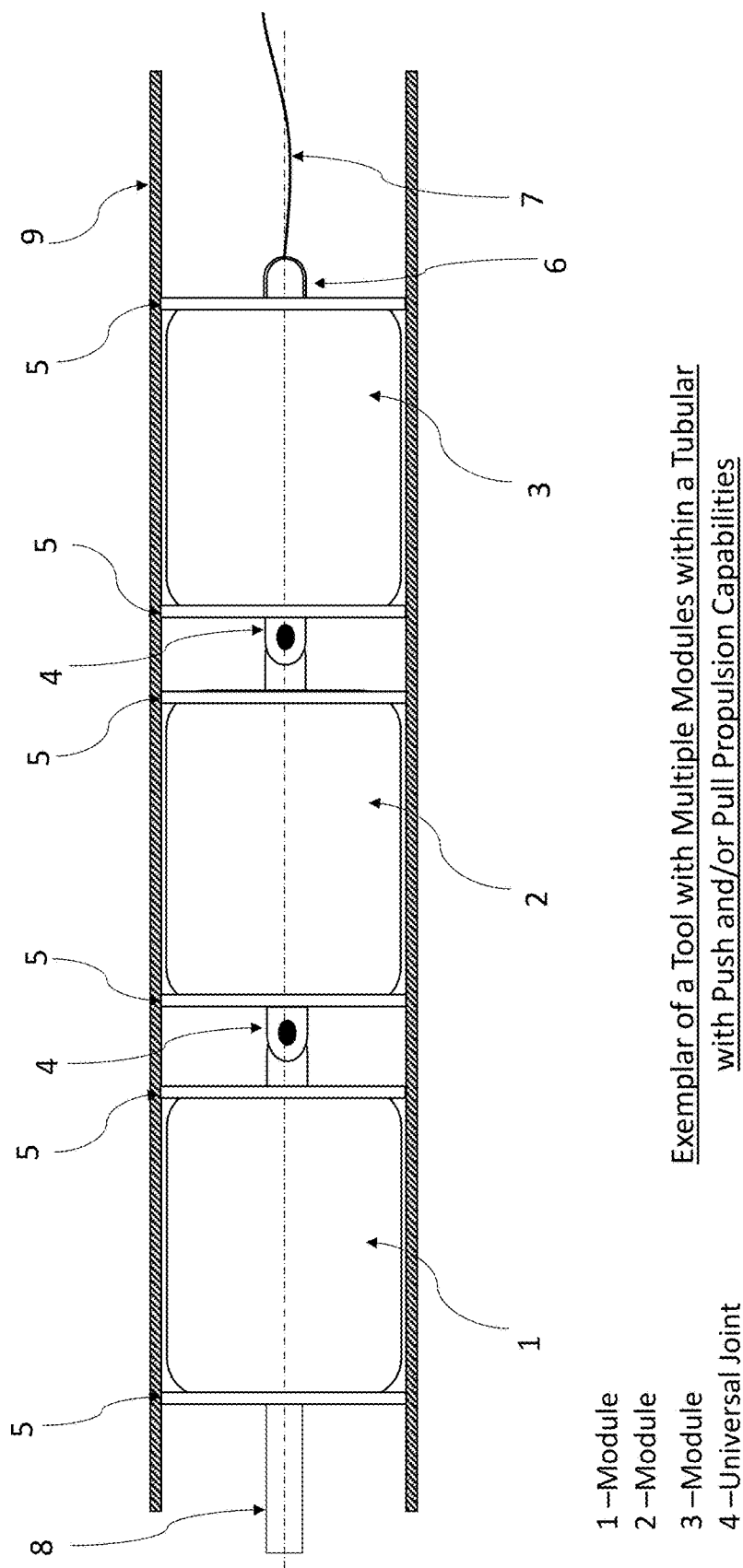
FIG. 3 shows a horizontal cross section of a pipe or tubular with another tool of the present invention disposed therein.

Optionally, a tool with multiple modules (such as shown in FIGS. 1-3) may contain multiple sensing technologies that interact with each other, and/or utilize shared componentry. For example, a tool with multiple modules may contain a single sensing technology that interacts between multiple modules, or a tool with multiple modules may include multiple sensing technologies that interact between the multiple modules.

The tool is self-propelled (such as, but not limited to, a robotic crawler, such as shown in FIG. 2), or may be propelled by a gaseous or liquid medium pressure differential (such as with a drive cup or the like as shown in FIG. 1), or is propelled (pulled) via a cable in tension (FIGS. 2 and 3), or is propelled (pushed) via a coiled tube in compression (FIG. 3), or a combination of the aforementioned propulsion means (see FIG. 3). The tool may be powered on-board, remotely, or a combination of both. Optionally, the tool may have a system and method to clean surfaces for better sensing abilities, incorporated with at least one module if utilized in the tool.

The tool of the present invention is preferably configurable so as to be operated in a wide variety of diameters or cross-sectional areas of conduits or pipes or the like. The tool may be attached to other tools (such as one or more other tools for crack detection, magnetic flux leakage, calipers, and/or the like).

The tool may simultaneously use the aforementioned (and below discussed) sensing technologies with an existing tool's sensing capabilities and/or system(s). For example, the MI sensing technologies may utilize crack detection sensing capabilities simultaneously through shared componentry, magnetic fields, perturbation energy, waves, and/or the like.

The tool preferably includes the means to determine the tool's position or location in a conduit or distance from a particular location, such as via, but not limited to, global positioning system(s), gyroscopic systems, encoders, and/or the like. Optionally, the tool may store such position/location/distance data on-board or may transmit the data to a remote location, or may perform a combination of both. Optionally, and desirably, the tool may combine the position/location/distance data simultaneously with sensing data collection at any discrete location within the tubular, whereby the system may determine or identify the material or other characteristics of the pipe or conduit at specific locations along the pipeline, which is useful in determining where sections of pipe may be made of a different material (such as when sections of pipe are replaced with pipes/conduits that are not of the same material as the rest of the pipeline).

Figure 4:
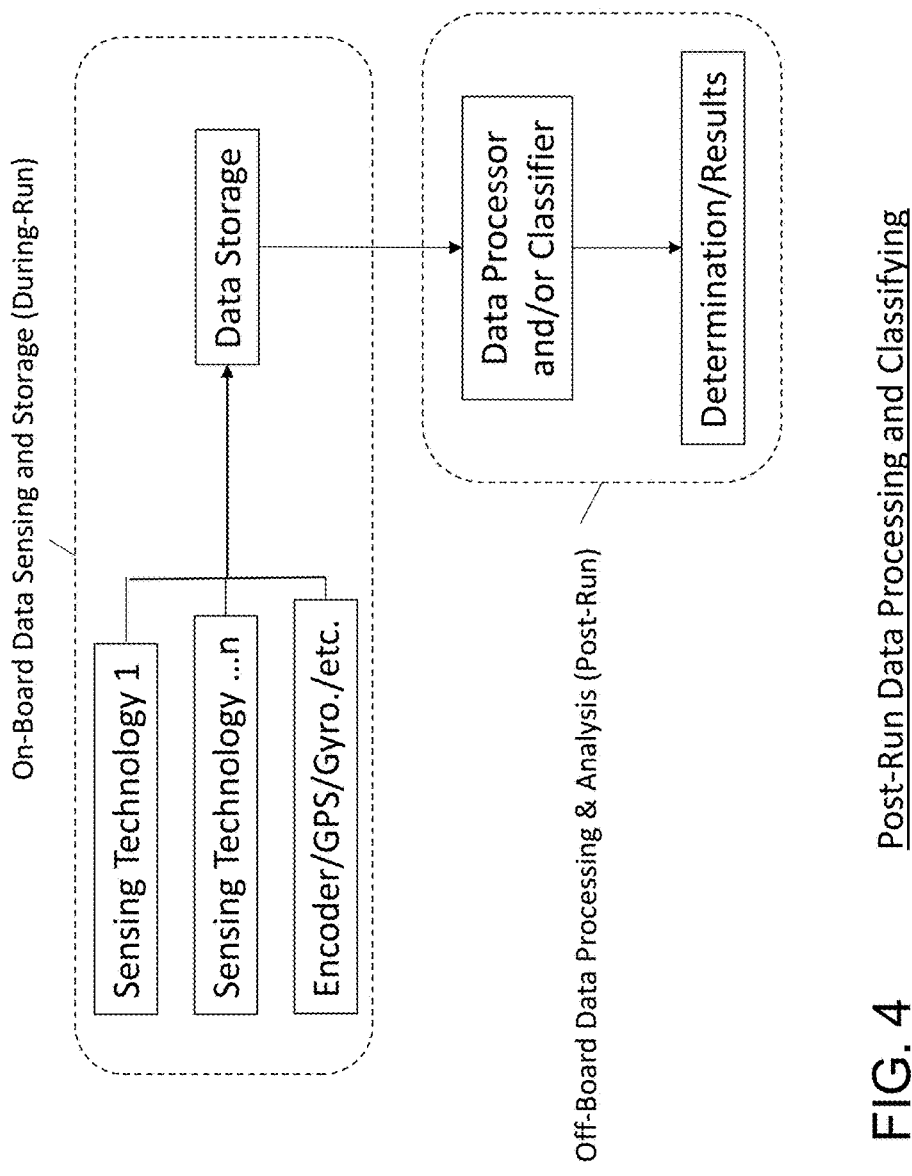
FIG. 4 is a block diagram showing processing and classifying stages of the system of the present invention.

As shown in FIG. 4, the tool includes on-board data sensing and storage, with one or more sensing technologies and optionally with GPS or other location/distance determining systems. As the tool travels along and within the pipe or conduit, the tool collects data via its sensing technologies and stores the data, whereby the stored data may be processed and classified and analyzed to determine the pipe material at an off-board data processing and analysis station (after the tool has completed its travel through the pipeline).

Figure 5:
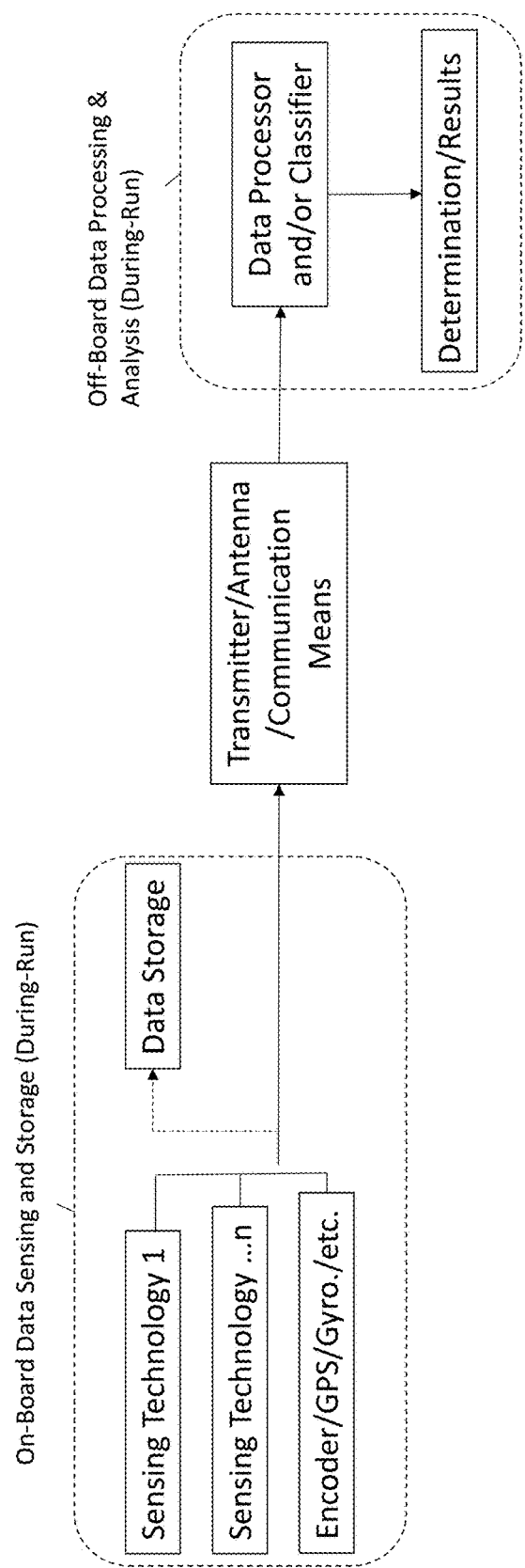
FIG. 5 is another block diagram showing real-time remote processing and classifying of data in accordance with the present invention.

Optionally, and such as shown in FIG. 5, the system may provide real-time data processing, with the data that is collected by the tool's sensing technologies is transmitted or communicated to an off-board data processing and analysis station so the results can be determined as the tool is still traveling through the pipeline.

Figure 6:
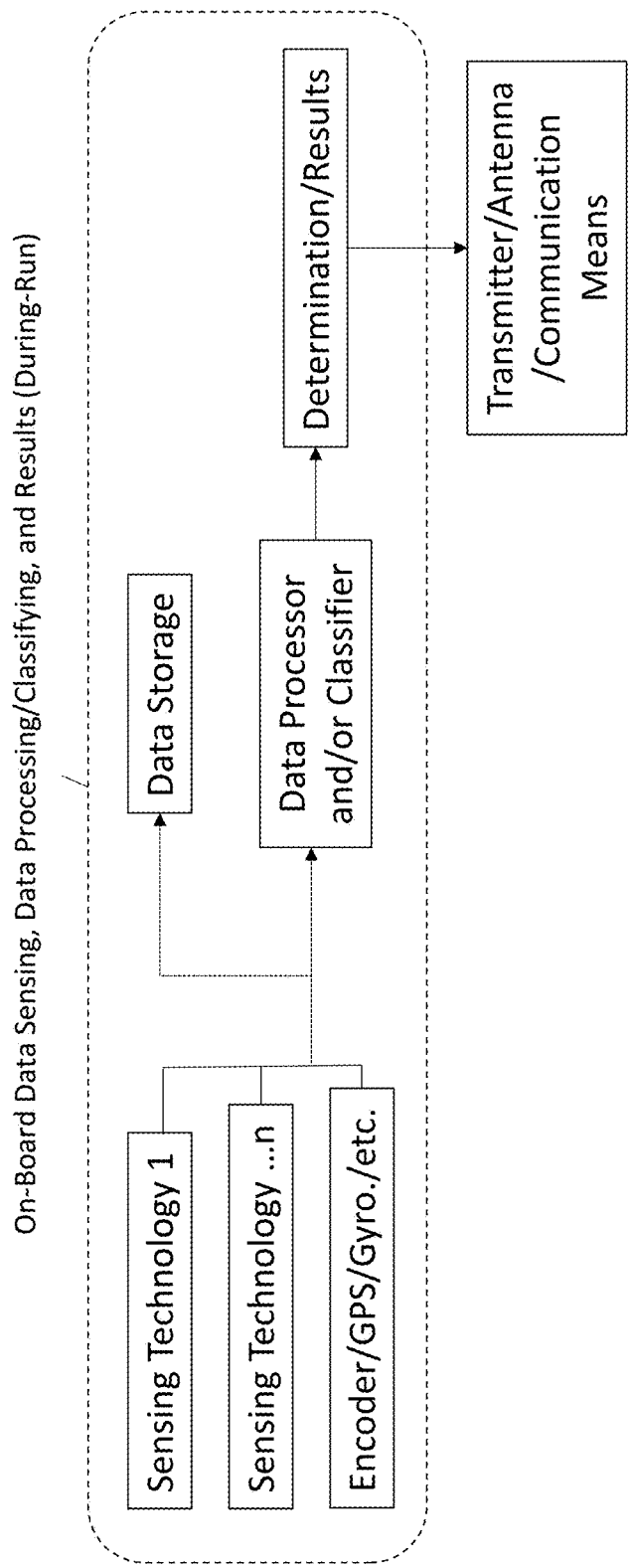
FIG. 6 is another block diagram showing real-time processing and classifying of data in accordance with the present invention.
Figure 7:
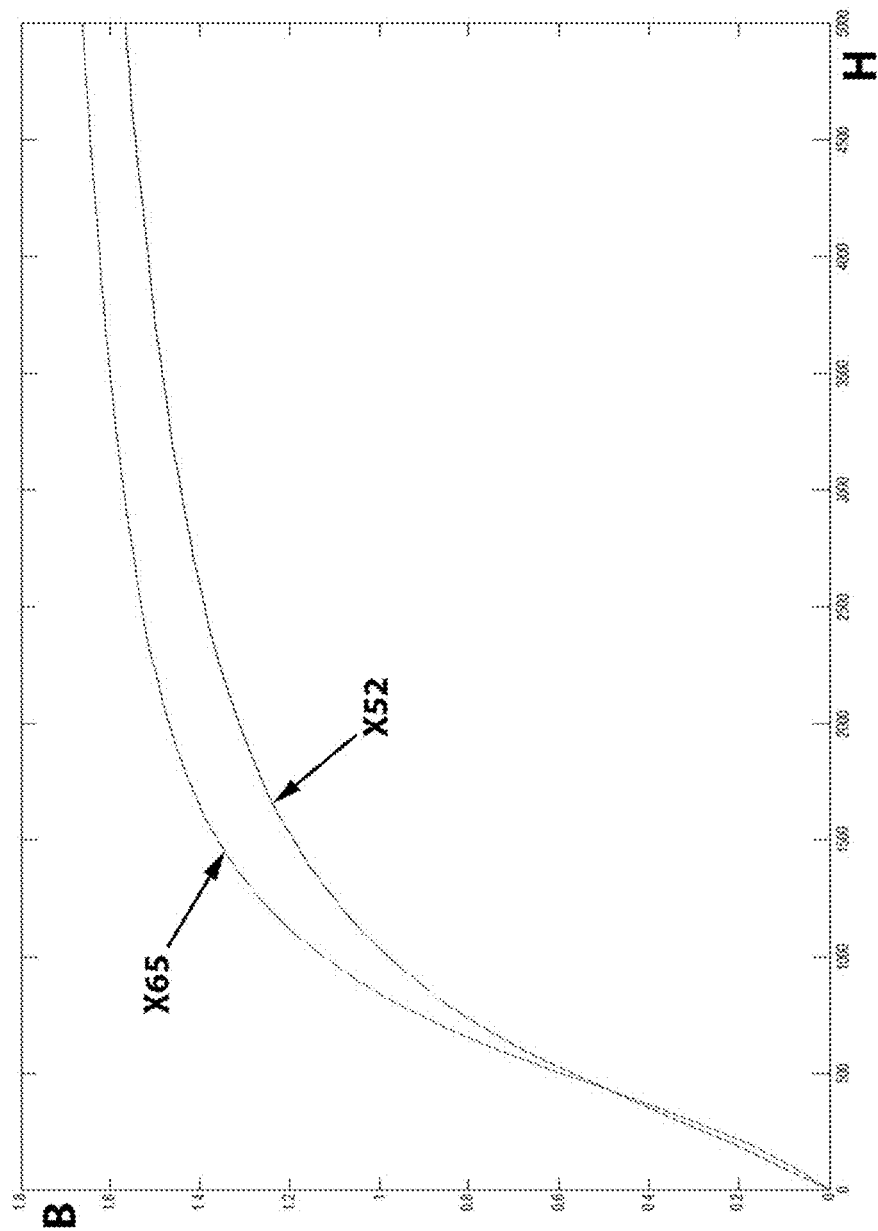
FIG. 7 is a B-H graph comparing changes in magnetic flux density (B) over magnetic field strength (H) for two grades of pipe.
Figure 8:
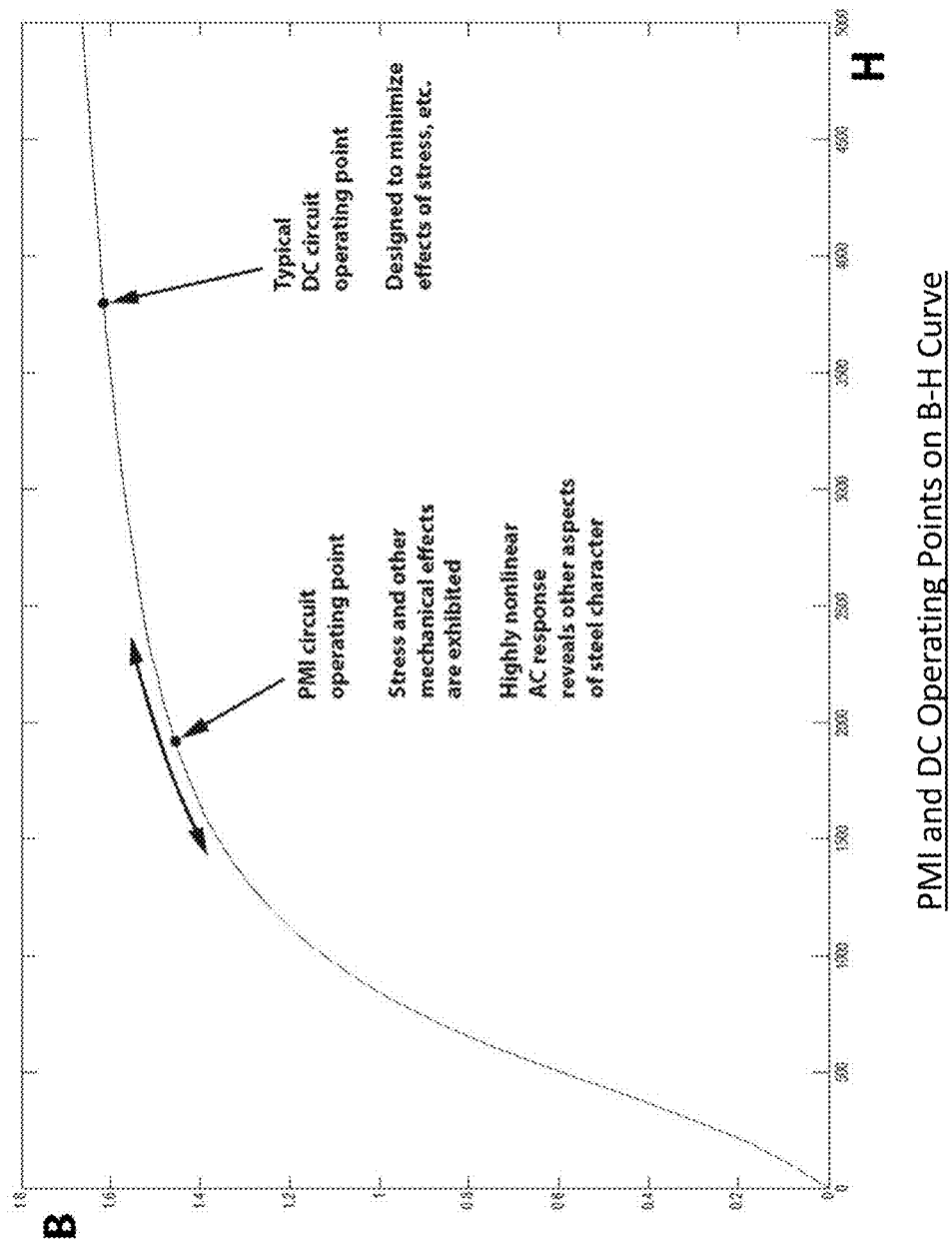
FIG. 8 is a B-H graph showing MI and DC operating points on the B-H curve.

Optionally, and such as shown in FIG. 6, the tool may include real-time data processing and analysis to determine the pipe material as the tool is traveling through the pipeline. In such an embodiment, the processing/analysis software is included in the tool itself, whereby only the determination or results is transmitted or communicated to a remote location (and the communicated results may include the material identification and the location along the pipeline associated with the identification, so that it can be known where the pipe material may change along the pipeline).

The tool and system and method collect and process/analyze data to determine physical properties of a conduit and to determine potential materials for each type of data collected or physical property determined. When it is determined that one or more of the determined physical properties are indicative of a particular type of material, the system determines or identifies the tubular as being constructed of that material.

For example, the system may utilize three sensing methods independently for positively identifying the material, such as Magnetic permeability measurements (MFL sensor), eddy current's current amplitude (PEC background measurements), and MBN hardness measurements. The system may be able to bin and characterize pipe materials with any of these technologies independently, but using two or more of the sensing methodologies increases the accuracy of the system in the material identification. The system may utilize PEC and/or MBN sensing methodologies independently or in combination, while remaining within the spirit and scope of the present invention. In an exemplary and preferred embodiment, the MFL technique may be run with another technology, such as either PEC or MBN, but it is envisioned that all three methodologies may be run together. By measuring different characteristics or physical properties of target materials with each sensing technology, the system may achieve higher correlations if multiple technologies are run and processed together.

Figure 9:
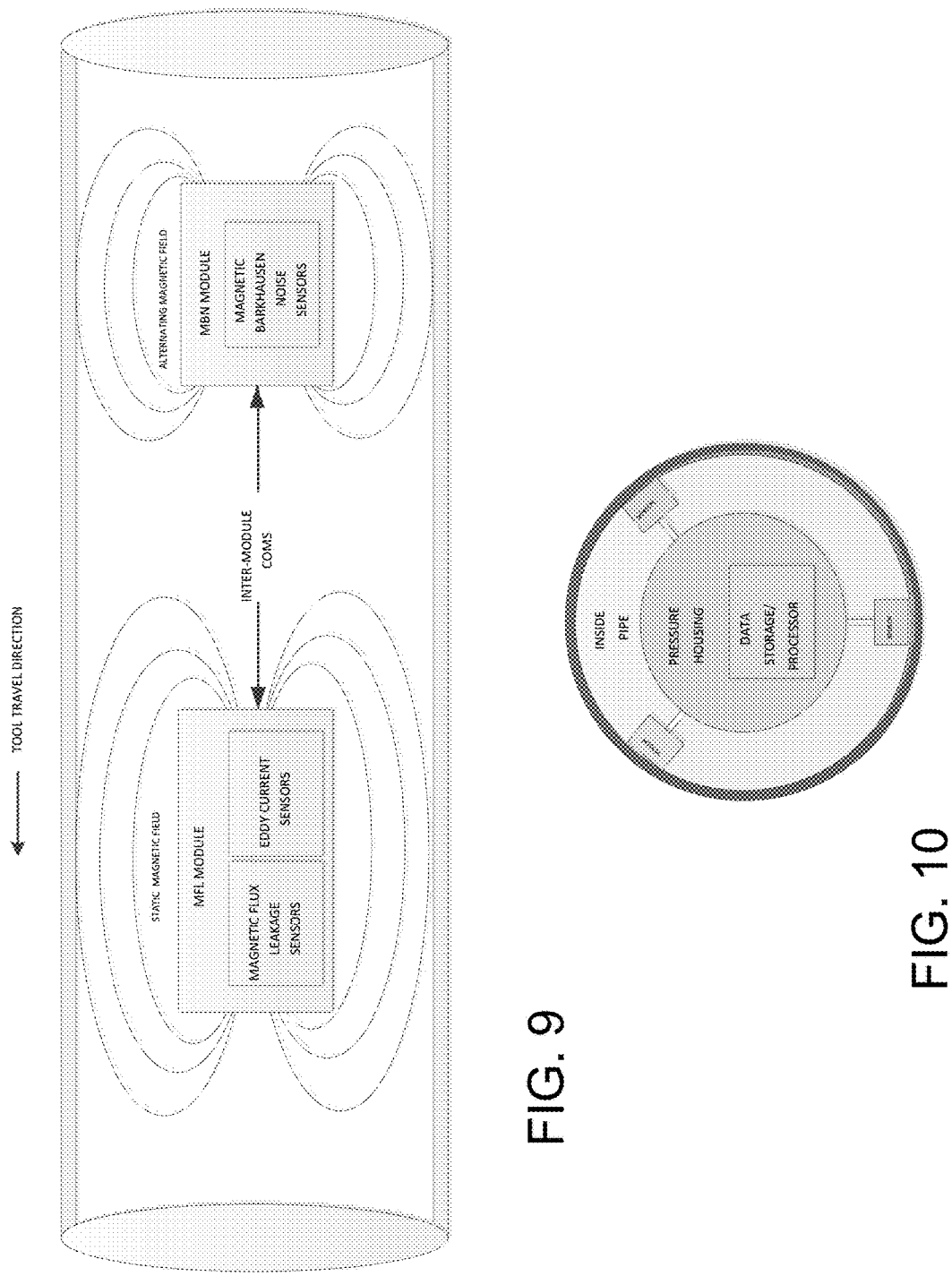
FIG. 9 is a schematic showing three sensing methodologies used to sense characteristics of a tubular to determine the material of the tubular in accordance with the present invention.
Figure 10:
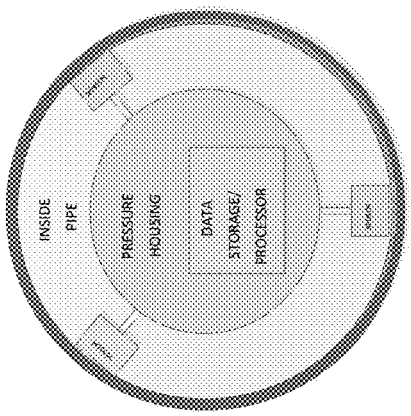
FIG. 10 is an end view schematic of a sensing system of the type shown in FIG. 9.
Figure 11:
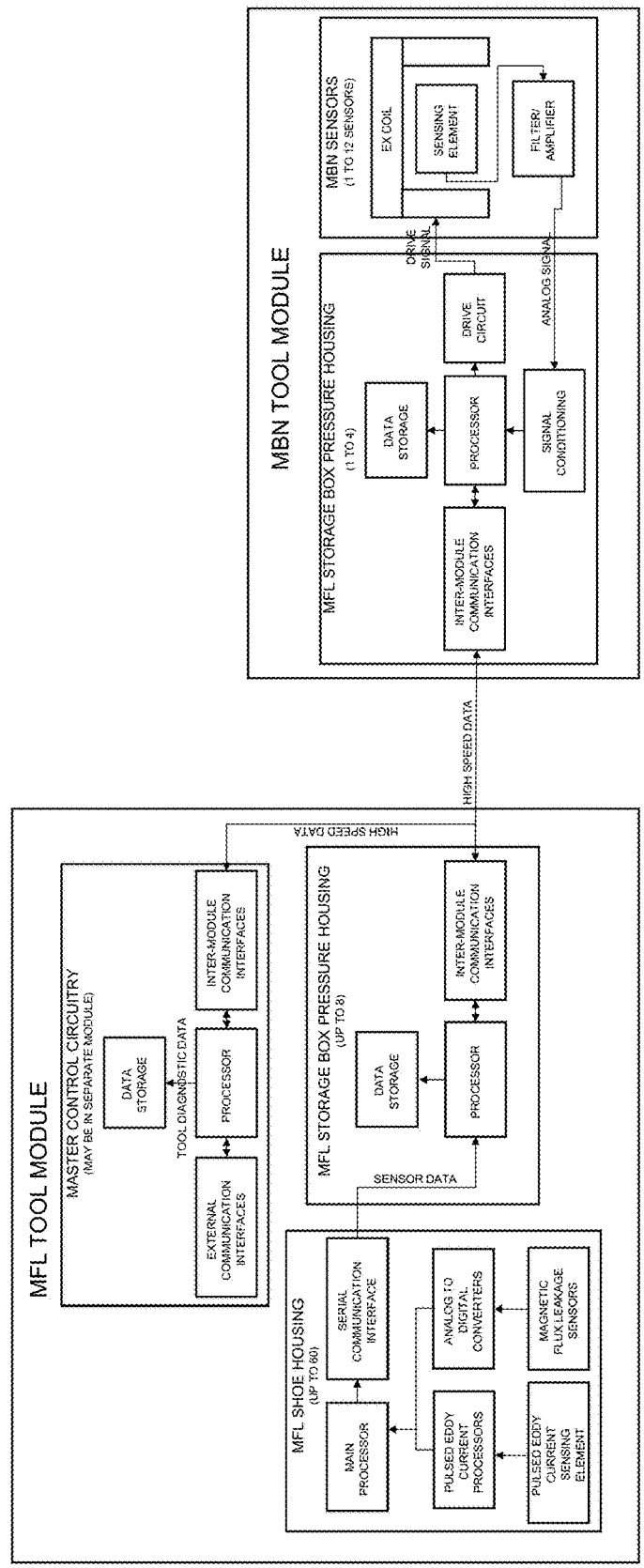
FIG. 11 is a block diagram of the sensing system of the type shown in FIG. 9.

If MFL techniques are used, the system may apply a magnetic field to the pipe to make it work. With PEC and MBN, magnetization is optional. PEC will work better in a magnetized field but may also or otherwise work in a zero field situation. However, it is not desirable to run MBN technology in a saturated field, so the tool may be operable to run MBN technology in a residual magnetic field (i.e., in a separate MBN sensing module that is towed behind an MFL tool). For example, and such as shown in FIGS. 9-11, the tool may include an MFL module followed by an MBN module, which follows a sufficient distance behind the MFL module so as to not have its sensing interfered with by the magnetic field of the MFL module. Because the MBN module needs to be spaced from the MFL module, the overall module would need to space the modules sufficiently apart or two separate modules may be used and run through the pipe sufficiently far apart, whereby the data may be correlated for any given sensing location along the pipe, such as via time and location stamping as the data is collected by both modules.

Figure 12:
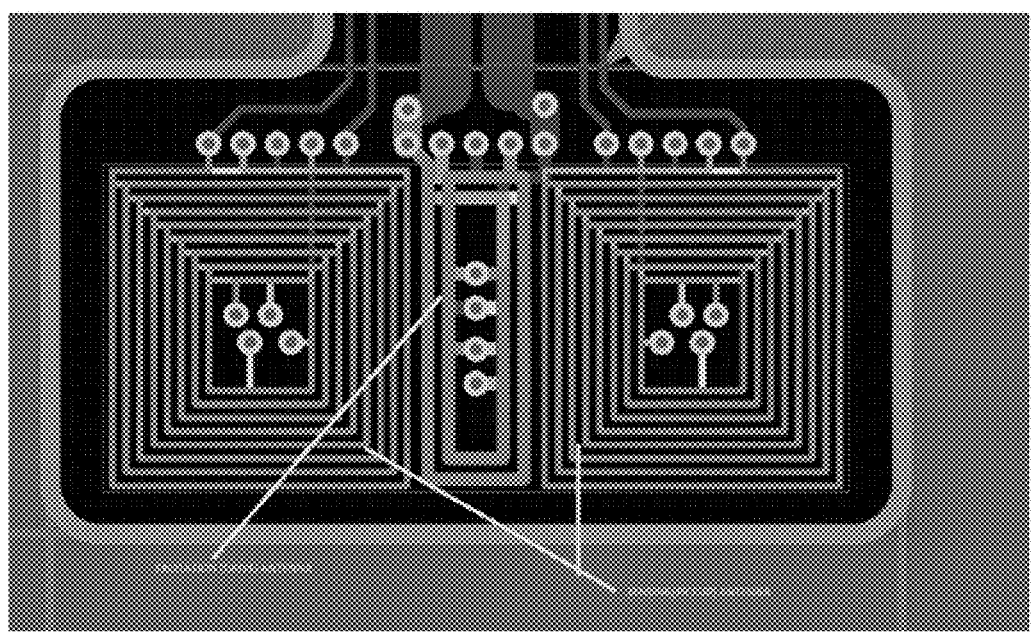
FIG. 12 is a plan view of a sensor antenna and excitation antenna arrays of a PEC sensor suitable for use in the system of the present invention.

Optionally, the system may utilize PEC sensing to determine and measure eddy currents deep into the wall of the tubular. The system (see sensor antenna and excitation antenna arrays of FIG. 12) may utilize a wide band of frequencies of electromagnetic pulses at the target material with some electric drive circuitry. The PEC excites eddy currents in the target material at many depths. The pulse is translated in to electrical current when it hits the target material (this is the eddy current). With a separate set of circuitry, that has its own separate sensing elements, it measures the magnetic field created by those eddy currents. The result is an aggregate of these eddy currents at multiple depths, which makes the PEC sensing suitable for material identification.

The signal that is measured directly correlates to the aggregate of the eddy current flows. Each sensing antenna is effectively its own self-contained Pulsed Eddy Current sensor. The drive circuitry can push current through a center drive antenna for a short period of time. The drive signal has effectively a great many of frequency harmonics in it. Each of those harmonics in the drive signal create eddy currents at different depths of the target metal.

With a short time delay, what is sensed is a complex waveform also with harmonics in it. This waveform is a multitude of resulting eddy currents. Depending on the metal composition and depths of eddy currents, there sensed signals will have a certain amplitude in a certain frequency domain. Thus, various materials can be identified when the sensed waveform correlates to that type of material.

Optionally, with the MBN sensing methodology, the MBN sensor or module can use what is essentially an electro magnet that is driven with an AC waveform, normally a sinewave, to generate the MBN effect. The system then measures the field created by the domains flipping in polarity, with the domains flipping with different intensity and at different speeds. The peak to peak amplitude of the pulses and the RMS have good material hardness correlation and thus can be used to determine or identify the material. This technology again measures the metal all the way through the pipe, not just slightly (such as a couple of millimeters or less) into the metal wall of the pipe.

With respect to MBN sensing methodologies, there are multiple characteristics of MBN that make it suitable for material identification applications. Magnetic Barkhausen Noise (MBN) is a phenomenon that occurs when a magnetic field in a ferrous material changes polarity. The domains that are in that ferrous material do not flip in a linear fashion. Instead, they avalanche shortly after the field flips polarity. The resulting magnetic fields from the flipping domains is the MBN. While it is very small, it can be sensed reliably with electronics. Due to the properties of magnetic domains in metals, the domains behave differently in materials of different hardness or stress. As different grades of inline pipe are of different hardness, the materials of those pipes can be identified with MBN sensors, either alone or in combination with one or more other sensing methodologies. The MBN signal changes as it encounters changing stress or hardness, and higher stress alters the magnetic domain behavior in ways that will create an amplified or damped MBN response. At the simplest level, a harder material will result in a different sized peak to peak signal measurement than a softer material with the same excitation level in a similar material.

The MBN signal contains a great deal of information. Most commercial applications of MBN use this data in its most elementary forms, such as peak to peak and signal RMS. There is more data in the MBN signal/response that can be analyzed revealing insight into material makeup and condition.

Optionally, the system may utilize distortion analysis of magnetic excitation (DAME) as an addition to an MBN sensor. Such distortion analysis of magnetic excitation (DAME) is a measurement approach for evaluation of different properties of ferromagnetic materials. The presence of a different ferromagnetic material introduces non-linear distortion in the excitation voltage across a coil around an electromagnetic yoke. The non-linear distortion behavior of the magnetic excitation voltage is influenced by the magnetization behavior of the ferromagnetic material between the poles of the electromagnetic yoke. The time derivative of the excitation voltage (dVE/dt) plotted as a function of total applied voltage (which is directly proportional to the applied magnetic field) has been found to show unique shape for each sample with different material conditions. The shape of the DAME profile with a peak and trough clearly reflects the subtle changes in the composition, microstructure, grain orientation and stress through their effect on the magnetization process in the ferromagnetic material.

By utilizing DAME as an addition to an MBN sensor, the system can deal with skin depth and may be appropriate for pipe sizing. This method may provide a high confidence method of material identification by itself. Optionally, and desirably, the system may comprise a hybrid with MBN and DAME in one sensor. Optionally, the MBN signatures may identify the material and DAME may be used to determine the thickness of that material.

Because there is a close correlation between yield strength and hardness, and MBN determines hardness, the system can process MBN data to determine the material. The MBN data is processed differently for this determination as compared to stress determinations. Also, the system can process MBN data differently to look for permeability. The system then can cross-correlate the MBN permeability results with the MBN hardness results to determine the material via just an MBN sensor and associated data processing.

Figure 13:
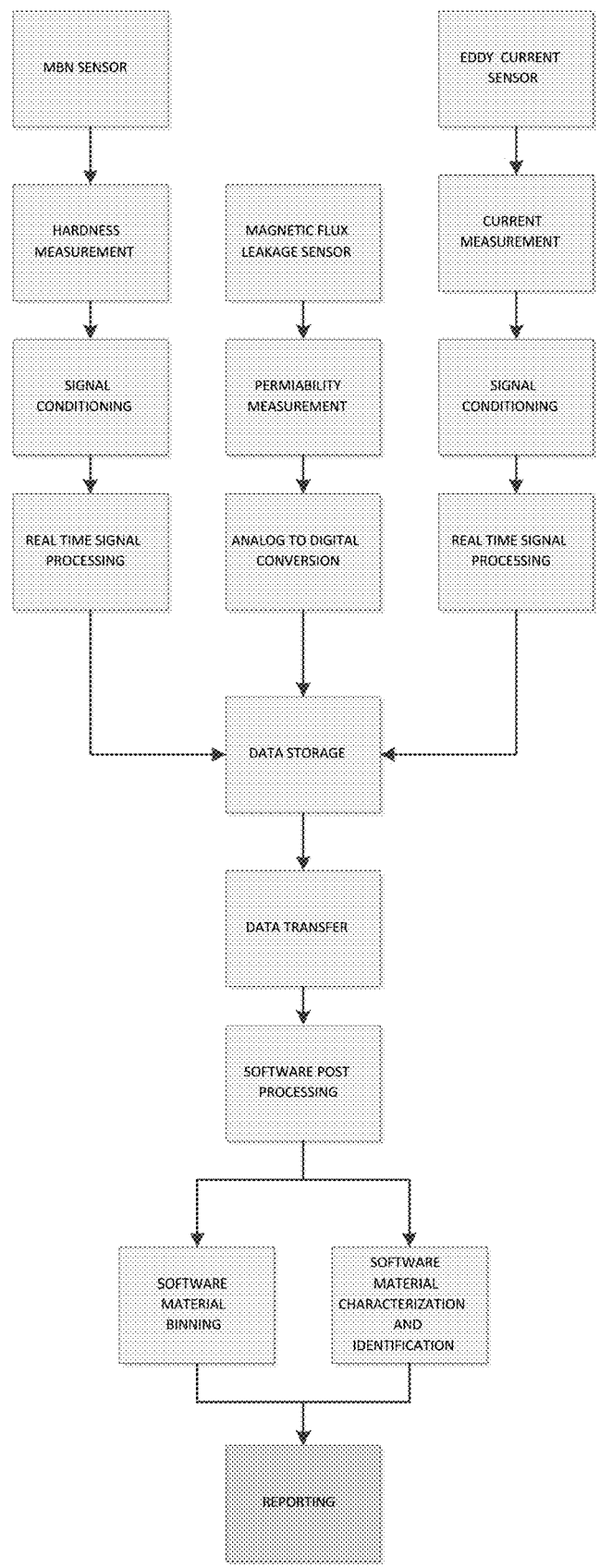
FIG. 13 is a flow chart of the sensing system of the present invention.

Therefore, the system of the present invention may utilize one (such as MBN) or more (such as MBN and permeability and/or PEC) sensing methodologies to determine or identify the material of the pipe or tubular. For example, and such as shown in FIG. 13, an MBN sensor may measure hardness, while an MFL sensor may measure permeability and/or an eddy current sensor may sense current within the pipe. The system may process the signals of each sensor to determine or identify the material. Optionally, the tool may store the data and correlate the data with a time and/or location when it was collected, and may process the data later to correlate the data and material properties. When the various measured characteristics correspond to a particular type of material, the system can, with a high degree of confidence, identify the particular type of material of the pipe or conduit or tubular.

For example, the sensed physical property data collected for various pipes will tend to group together for particular types of materials. The different types of material thus can be represented by different or respective bins of data points. Once data ranges are correlated for particular types of materials, the system can readily identify a material by processing and grouping data from one or more sensors. For example, if it is known that a particular type of pipe material is within a particular range of sensed values or characteristics for a particular physical property, then the system can identify or infer to a certain confidence that a measured or sensed material is that particular type of material when the system recognizes that particular range of sensed data for the sensed physical property.

The tool and system and method of the present invention thus provides for various sensing means to collect data that may be processed and correlated for use in determining or identifying the material of the pipe or conduit in which the tool is disposed. The sensing technologies used may comprise any suitable sensing technologies that are capable of sensing various material properties as the tool travels through the pipeline. For example, the sensing technologies implemented in the tool and method and system of the present invention may include one or more of the technologies discussed below.

Material Identification Technologies with Characteristics/Benefits/Methodologies The following provides a summary of various exemplary sensing technologies that the system of the present invention can utilize to collect data about a pipe or conduit, whereby the processor or processing techniques of the present invention may process the collected data to determine or identify the material of the pipe in which the tool is disposed.

Barkhausen Noise
    Hardness Measurement (e.g., such as in use in steel mills, etc.)
    Unique Pattern Analysis
    Unique Spectra to Hardness and (potentially) Strengths
    May utilize aspects of the systems described in U.S. Pat. Nos. 8,035,374 and/or 8,797,033, which are hereby incorporated herein by reference in their entireties.

Pulsed Eddy Current
    Broad bandwidth
    Provides other data/information within the signal
    More power efficient than low frequency AC (LF AC)
    Introduces a lot of high frequencies that create near surface eddy currents
    Provides information for processing/classifying.

Remote Field Eddy Current
    Similar to LF AC
    Performs many B-H experiments over-and-over, but looks at the far field rather than the near field
    Responds well to magnetic permeability (B-H curve)—related to yield strength
    Change in position of the receiver coil (compared to LF AC)
    Far field receiver position homogenizes the signal from the pipe which should minimize the effect of local variations (pitting, corrosion, hard spots, etc.)

Low Frequency AC (LF AC)
    Advantage is a less complex system (easy to build)
    B-H curve (hysteresis loop) related to yield strength
    Performs many B-H experiments over-and-over High Frequency AC (HF AC) Methods
    Giant Magneto-impedance (GMI) Sensing
    A magnetic permeability method
    Voltage readout directly correlates to hardness
    This could also be used for crack detection, or may be harvested from it being used in near-side crack and flaw detection purposes Impedance Methods (Single Transducer)
    A magnetic permeability method that can be incorporated with the LF AC or pulsed eddy current methods
    Requires no receiver
    May be incorporated with acoustic methods as well
    Utilizes the coupling between an energy generator (which could be the transmit coil or piezo stack from the RF EC, LF AC or acoustic measurement) and the pipe, which is viewed as a load on the generator.

Changes in the pipe character affect the load on the generator and can be detected in the energy generator's drive circuitry.

Acoustic

Various acoustic means and methods may be suitable to assist in determining or identifying the pipe material Acoustic velocity/acoustic attenuation relationships with yield strength and Young's Modulus Surface acoustic waves can determine hardness as attenuation has been shown in the past to be quite sensitive to a steel grade that has been subjected to various heat treatments, allowing attenuation to differentiate between various states of hardness Therefore, the present invention provides a tool or device that utilizes one or more sensing means to collect data pertaining to material properties of the pipe or conduit in which the tool is disposed. The collected data is processed and analyzed to determine or identify the particular material of the pipe at various locations along the conduit or pipeline. Thus, the system and method of the present invention can determine when a section of pipe has been replaced with a different material pipe, which may assist in determining or predicting weak points of future failure locations along a pipeline.

The system and method of the present invention processes data collected from different sensing means (such as, for example, from a Barkhausen noise sensor and an acoustic sensor and a low frequency AC sensor) and extracts information from the sensors' data to determine the material of the pipe being sensed. The system and method may look for information or properties indicative of particular materials and may correlate the data from the different sensing techniques to extract information that assists in accurately identifying the particular material of the pipe or conduit being sensed by the tool or device. Such a process and analysis is helpful in determining weaknesses or potential future weaknesses or failures at locations along the conduit or pipeline (such as by determining pipeline materials for some sections that may be more susceptible to types of failures, such as stress corrosion cracking, rupture, or the like).

Changes and modifications to the specifically described embodiments may be carried out without departing from the principles of the present invention, which is intended to be limited only by the scope of the appended claims as interpreted according to the principles of patent law including the doctrine of equivalents.

The invention claimed is:

1. A material property determining system operable to determine properties of a conduit, said material property determining system comprising:
a tool movable along a conduit and having at least one sensing device for sensing at least one property of the conduit;
a processor operable to process outputs of said at least one sensing device;
wherein said at least one sensing device senses a hardness of the conduit;
wherein said at least one sensing device senses a permeability of the conduit;
wherein, responsive to processing of the outputs by said processor, said processor correlates the processed outputs of the hardness of the conduit and the permeability of the conduit to determine the type of material of the conduit;
wherein the processor determines a set of types of material with the sensed hardness of the conduit, and wherein the processor determines the type of the material of the conduit with the sensed permeability of the conduit from the set of types of material.

2. The material property determining system of claim 1, wherein said tool comprises at least one module with each module having at least one sensing device.

3. The material property determining system of claim 1, wherein said tool comprises at least two modules with each module having at least one respective sensing device.

4. The material property determining system of claim 1, wherein said at least one sensing device comprises at least two sensing devices using different sensing technologies.

5. The material property determining system of claim 4, wherein said at least two sensing devices comprise at least two of (i) a sensing device that senses magnetic Barkhausen noise, (ii) a sensing device that uses pulsed eddy currents to sense properties of the conduit, (iii) a sensing device that uses remote field eddy currents to sense properties of the conduit, (iv) a sensing device that uses low frequency AC to sense properties of the conduit, (v) a sensing device that uses high frequency AC to sense properties of the conduit, (vi) a sensing device that uses impedance methods to sense properties of the conduit, and (vii) a sensing device that uses acoustic sensing means to sense properties of the conduit.

6. The material property determining system of claim 1, wherein said at least one sensing device comprises a sensing device that senses magnetic Barkhausen noise.

7. A method for determining a material of a conduit, said method comprising:
providing a tool having at least one sensing device for sensing at least two physical properties of the conduit, wherein the at least two physical properties comprise a hardness of the conduit and a permeability of the conduit;
moving the tool along the conduit;
providing a processor;
processing via the processor outputs of the at least one sensing device;
wherein, responsive to processing of the outputs by said processor, correlating the processed outputs of the hardness of the conduit and the permeability of the conduit to determine the type of material of the conduit; and
wherein correlating the processed outputs comprises:
determining, via the processor, a set of types of material with the sensed hardness of the conduit; and
determining, via the processor, the type of the material of the conduit with sensed permeability of the conduit from the set of types of material.

8. The method of claim 7, wherein the tool comprises at least one module with each module having at least one sensing device.

9. The method of claim 7, wherein the tool comprises at least two modules with each module having at least one respective sensing device.

10. The method of claim 7, wherein the at least one sensing device comprises at least two sensing devices using different sensing technologies.

11. The method of claim 10, wherein the at least two sensing devices comprise at least two of (i) a sensing device that senses magnetic Barkhausen noise, (ii) a sensing device that uses pulsed eddy currents to sense properties of the conduit, (iii) a sensing device that uses remote field eddy currents to sense properties of the conduit, (iv) a sensing device that uses low frequency AC to sense properties of the conduit, (v) a sensing device that uses high frequency AC to sense properties of the conduit, (vi) a sensing device that uses impedance methods to sense properties of the conduit, and (vii) a sensing device that uses acoustic sensing means to sense properties of the conduit.

12. The method of claim 10, wherein correlating the processed outputs comprises comparing the processed outputs to at least two known physical properties that correspond with the physical properties sensed by said at least two sensing devices using different sensing technologies to determine the type of material of the conduit.

13. The method of claim 7, wherein the at least one sensing device comprises a sensing device that senses magnetic Barkhausen noise.

14. The method of claim 7, wherein correlating the processed outputs comprises comparing the processed outputs to known physical properties to determine the type of material of the conduit.

* * * * *

UNITED STATES PATENT AND TRADEMARK OFFICE
CERTIFICATE OF CORRECTION

PATENT NO.        : 10,444,194 B2
APPLICATION NO.   : 15/495108
DATED             : October 15, 2019
INVENTOR(S)       : Bruce I. Girrell et al.

Page 1 of 1

It is certified that error appears in the above-identified patent and that said Letters Patent is hereby corrected as shown below:

Column 10
Line 48, Claim 7, "with sensed" should be --with the sensed--

Signed and Sealed this
Twelfth Day of November, 2019

Andrei Iancu
*Director of the United States Patent and Trademark Office*